United States Patent [19]

Bone

[11] 4,181,856

[45] Jan. 1, 1980

[54] ARRANGEMENTS FOR DETECTORS OF RADIATION

[75] Inventor: Phillip R. Bone, Hillingdon, England

[73] Assignee: EMI Limited, Hayes, United Kingdom

[21] Appl. No.: 881,814

[22] Filed: Feb. 27, 1978

[30] Foreign Application Priority Data

Mar. 24, 1977 [GB] United Kingdom ............... 12410/77

[51] Int. Cl.² ............................................. G01T 1/20
[52] U.S. Cl. ...................................... 250/366; 250/367
[58] Field of Search .................. 250/361 R, 366, 367, 250/369, 445 T

[56] References Cited

U.S. PATENT DOCUMENTS

| 3,944,833 | 3/1976 | Hoonsfield ............................ 250/367 |
| 4,070,581 | 1/1978 | Gibbons et al. ................... 250/445 T |

*Primary Examiner*—Davis L. Willis
*Attorney, Agent, or Firm*—Cooper, Dunham, Clark, Griffin & Moran

[57] ABSTRACT

An ionizing radiation detector arrangement includes scintillator crystals and respective photodiodes of elongate form and mountings to assemble these in sub-arrays of, for example, four, units. The mountings are shaped to permit assembly around a ring with radially extending cards bearing circuit components. Assembly is made accurately by including skewed lugs in the mountings.

1 Claim, 6 Drawing Figures

ARRANGEMENTS FOR DETECTORS OF RADIATION

The present invention relates to arrangements for detecting ionising radiation, such as X-radiation, and it relates more specifically to such arrangements as may include several individual detectors in close proximity to one another.

A requirement for such arrangements exists, for example, in the field of computed tomography (CT) wherein radiation projected across a cross-sectional slice of a body under examination along a great many substantially linear beam paths is detected after emergence from the body. The radiation emanates from a source which is scanned, relative to the body, around, and possibly also across, the aforementioned slice. The radiation emergent from the slice is detected possibly by means of a single detector, but more usually, nowadays, by means of a bank of detectors which may or may not scan relative to the body.

CT scanners utilising a bank of detectors require that the detectors be ruggedly mounted and that neighbouring detectors be closely adjacent one another. It is an object of this invention to provide a detecting arrangement which satisfies the above criteria.

Where a great many detectors are to be provided, not only the detecting arrangements themselves, but also the mounting means therefor have to be economical and another object of this invention is to provide an economic mounting arrangement for a plurality of detectors. Also, in circumstances where a large number of detectors are provided in an array it is desirable that the array be built up from sub-arrays, each containing a few detectors (of the order of ten), and that the sub-arrays can be removed individually for servicing or replacement. Another object of the invention is to provide a detecting arrangement which includes this desirable feature.

According to the invention there is provided an arrangement for detecting ionising radiation comprising a plurality of detector devices, each for receiving said radiation and for producing electrical output signals indicative of the amounts of radiation so received, a plurality of detector holders, each supporting a plurality of said devices, a locating block, means securing said holders in said block so that said neighbouring ones of said detector devices are disposed closely adjacent one another, presenting a substantially continuous receiving surface to said radiation, a printed circuit card, including at least a respective amplifier for the electrical signals produced by each of said devices, and connector means secured to said locating block, making respective connections between said devices and said card.

Embodiments of the invention will now be described with reference to the accompanying drawings, in which.

Figure 1:
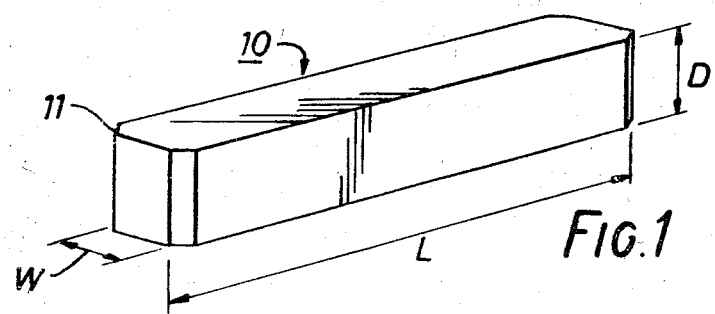
FIG. 1 shows a scintillation crystal.
Figure 2:
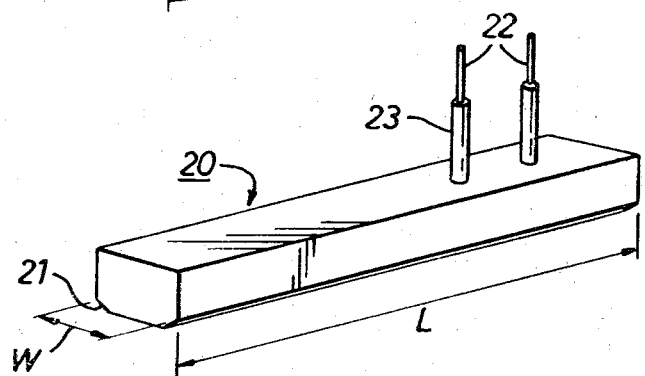
FIG. 2 shows a semiconductor photo-diode which may be used in co-operation with the crystal shown in FIG. 1.

FIG. 1 shows an elongated crystal 10 of caesium iodide (doped with thallium). The radiation is intended to fall upon the uppermost face of the crystal. In that case, if the crystal is intended for use in a CT system, the dimension 'L' lies perpendicular to the cross-sectional slice of the body under examination and the dimension 'W' represents the width of the detector in the cross-sectional slice. The crystal depth "D" must be enough to absorb substantially all of the radiation incident upon the crystal in order that efficient use can be made of the radiation administered to the body. For this reason, very little radiation will emerge from the lower surface of the crystal and it is thus possible to fix a photo-diode, shown at 20 in FIG. 2, to the said lower surface without the need for shielding.

Figure 3:
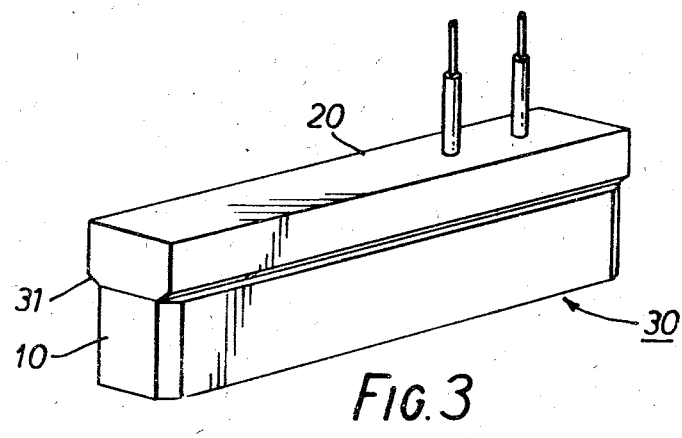
FIG. 3 shows a detector device comprising, in combination, the crystal of FIG. 1 and the photo-diode of FIG. 2, FIGS. 4 and 5 show two views of sub-assembly of detector devices

The photo-diode 20 shown contains the semiconductor elements of one long thin diode. Alternatively, however, the diode 20 can be replaced by a number of smaller diodes wired in parallel, series or a series/parallel combination to suit the application. Normally the photo-diode 20 is encapsulated in a plastic package and is glued with optical cement 31 (FIG. 3) to the crystal 10. The front face of the diode is chamfered, as at 21, along its length on both sides to take up any excess cement and ensure the production of a strong bond between the diode and the scintillation crystal. Two leads 22, with insulation 23, are brought out of the rearward surface of the diode. The leads are placed towards one end of the diode surface to make identification easy.

The photo-diode and scintillation crystal form a detector device 30 which is covered all over with a suitable paint (normally white) to improve the optical coupling between the elements of the device. The detector device is then either covered with a protective resin, or with silicon grease, to provide a barrier against moisture (not shown).

Figure 4:
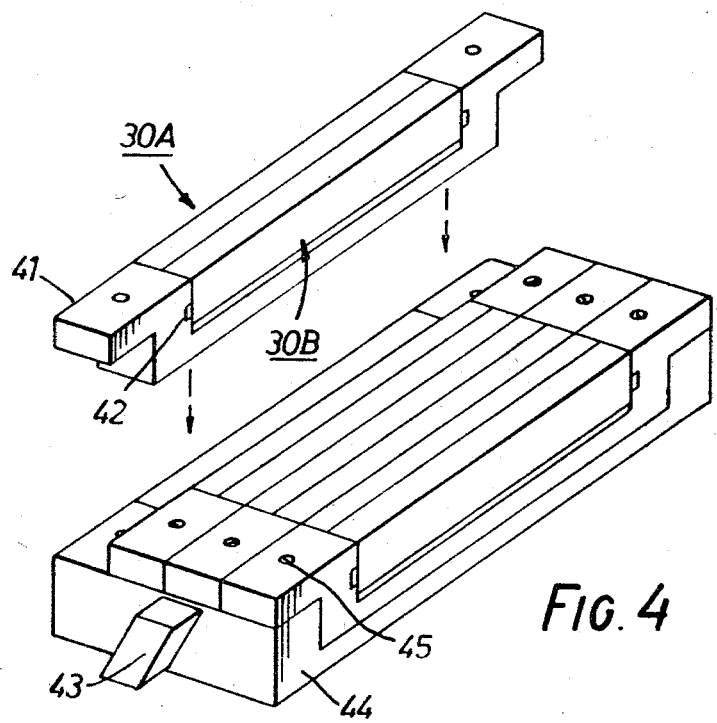
Figure 5:
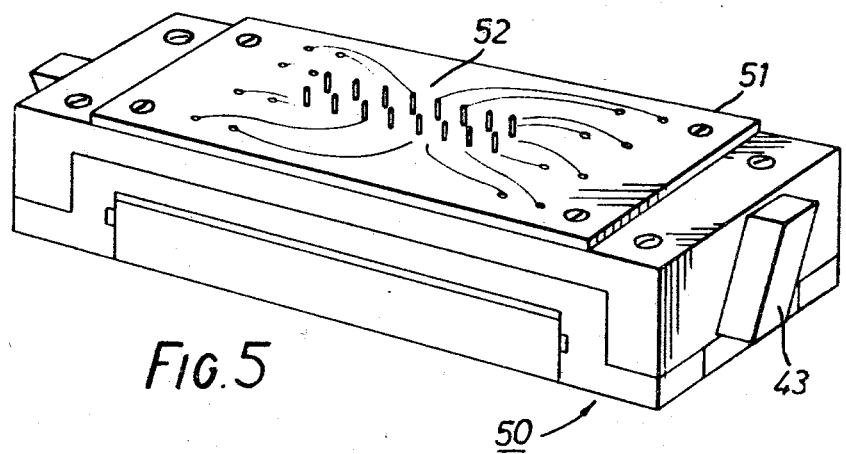
Figure 6:
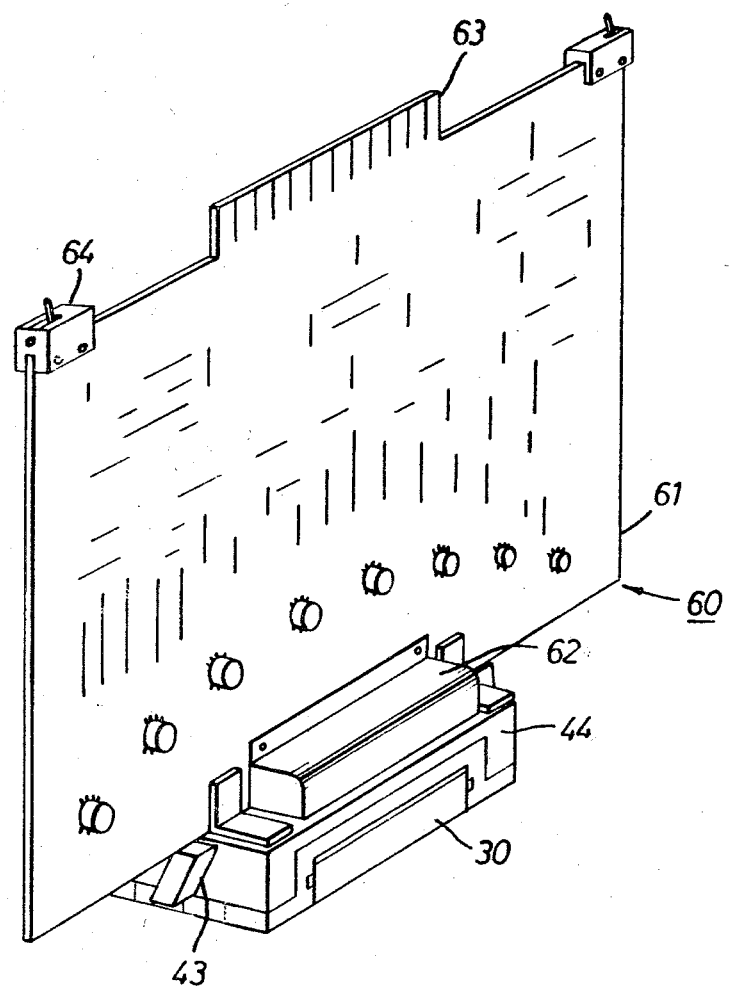
FIG. 6 shows the sub-assembly of FIGS. 4 and 5 with additional components.

The detectors such as 30 are typically potted in pairs such as 30A and 30B (FIG. 4) into holders such as 41. The holders have slots 42 milled in the recesses to provide a 'Key' for a potting resin.

The detector holders 41 are screwed as shown at 45 into a locating block 44. Normally a block supports four holders each containing two detector devices.

The photo-diode leads pass through the holder 41 and locating block 44 where they are soldered onto a small circuit board 51 which constitutes a connnector means and routes these connections onto a line of pins 52. These pins are connected with stiff wire to a corresponding line of pins on a printed circuit card 61 which contains at least a respective amplifier for each detector device and is mounted at right angles to the connecting board 51. A screen 62 covers the connections between the pins 52 and the card 61.

The card 61 conveniently contain, as well as the photo-diode current amplifiers, gain controls and calibration controls as required by a CT machine. Other connections to or from the card 61 are made via an edge connector 63 which can be sited anywhere around the board but is normally on the end opposite the connections to the board 51.

The whole detector assembly 60 is slid into the detector stack or array along guides and accurately lined up; locating lugs 43 protruding from the locating block and engaging suitable slots (not shown). The lugs 43 may be vertical, instead of being canted as shown. The amplifier card maintains alignment of the whole assembly by virtue of spring-loaded catches 64.

Several of these detector assemblies can be used to form a larger array of detector devices. To reduce the possibility of X-rays leaking from one detector to another, shims of an X-ray screening material, such as tantalum, can be used between the detectors.

Detectors constructed in accordance with the techniques described above are useful in CT machines where an array of an arc or circle of detectors is required with the detectors close together to present a substantially continuous receiving surface to said radiation.

It will be appreciated that the scintillation material used need not be caesium iodide. There are a number of other materials which are readily available and could be used instead of caesium iodide. Some such materials are Bismuth Germanate, Gadolinium oxy-sulphide, cadmium tungstate and sodium iodide.

I claim:

1. An arrangement for detecting ionising radiation including a plurality of scintillator crystals, a plurality of photo-diodes, the crystals being secured to, and in direct optical communication with, respective ones of said photo-diodes, to form a plurality of detectors adapted to produce electrical output signals in response to ionising radiation incident on said crystals, a plurality of detector holders each constructed to receive a respective pair of said detectors and to support said detectors in side-by-side relationship with adjacent edges of the respective crystals in contact, a locating block constructed to receive said holders and to locate the respective detectors supported by said holders with the crystals of all adjacent detectors in contact, presenting a substantially uninterrupted receiving surface to said ionising radiation, said locating block being formed with projecting lugs for location of the complete assembly in relation to other similar assemblies.

* * * * *